United States Patent
Jenkins et al.

(10) Patent No.: US 6,190,173 B1
(45) Date of Patent: Feb. 20, 2001

(54) METHOD AND APPARATUS FOR TRAINING OF AUDITORY/VISUAL DISCRIMINATION USING TARGET AND DISTRACTOR PHONEMES/GRAPHICS

(75) Inventors: William M. Jenkins, Pacifica; Michael M. Merzenich, San Francisco; Steven L. Miller, Pacifica; Bret E. Peterson, Lafayette, all of CA (US); Paula Tallal, Lumberville, PA (US)

(73) Assignee: Scientific Learning Corp., Berkeley, CA (US)

( * ) Notice: Under 35 U.S.C. 154(b), the term of this patent shall be extended for 0 days.

(21) Appl. No.: 09/089,149

(22) Filed: Jun. 2, 1998

Related U.S. Application Data

(63) Continuation-in-part of application No. 08/982,189, filed on Dec. 17, 1997, now Pat. No. 5,927,988.

(51) Int. Cl.[7] .................................................. G09B 5/00
(52) U.S. Cl. ........................ 434/169; 434/167; 434/185; 434/307 R; 706/16; 704/270; 704/503; 704/504
(58) Field of Search .................................... 434/116, 118, 434/156, 157, 169, 185, 307 R, 308, 323, 362, 365; 706/16, 927; 704/222, 270, 243, 265, 503, 504; 345/473, 952, 956

(56) References Cited

U.S. PATENT DOCUMENTS

| | | | |
|---|---|---|---|
| 3,920,903 | * 11/1975 | Beller ................................... | 434/185 |
| 5,170,432 | * 12/1992 | Hackbarth et al. ................... | 704/254 |
| 5,799,267 | * 8/1998 | Siegel ....................................... | 704/1 |
| 5,813,862 | * 9/1998 | Merzenich et al. ................... | 434/185 |
| 5,873,061 | * 2/1999 | Hab-Umbach et al. ............. | 704/254 |
| 6,071,123 | * 6/2000 | Tallal et al. ........................... | 434/116 |
| 6,076,060 | * 6/2000 | Lin et al. .............................. | 704/260 |
| 6,078,885 | * 6/2000 | Beutnagel ............................ | 704/258 |
| 6,094,633 | * 7/2000 | Gaved et al. ......................... | 704/260 |

FOREIGN PATENT DOCUMENTS 0 534 410 A2  *  3/1993 (EP) .

\* cited by examiner

Primary Examiner—Joe H. Cheng
(74) Attorney, Agent, or Firm—James W. Huffman

(57) ABSTRACT

An apparatus and method for training of auditory and graphical discrimination in humans is provided. The method and apparatus provides a number of stimulus sets, each stimulus set having a target phoneme, and associated grapheme, and a number of distractor phonemes, and associated graphemes. Upon initiation of a trial, a target phoneme is presented to a subject. A stimulus stream is then prepared that consists of a random sequence of distractor phonemes. Located within the sequence of distractor phonemes is the target phoneme. The stimulus sequence is presented to the subject for identification of the target phoneme within the sequence. Speech processing is used to provide multiple levels of emphasis for enhancing a subject's ability to discriminate between similarly sounding phonemes. The processing is applied to the presentation of the target phoneme and the stimulus stream. As a subject correctly identifies target phonemes within stimulus streams, across all provided stimulus sets, the amount of processing applied to the phonemes is reduced, ultimately to the level of normal speech.

21 Claims, 10 Drawing Sheets

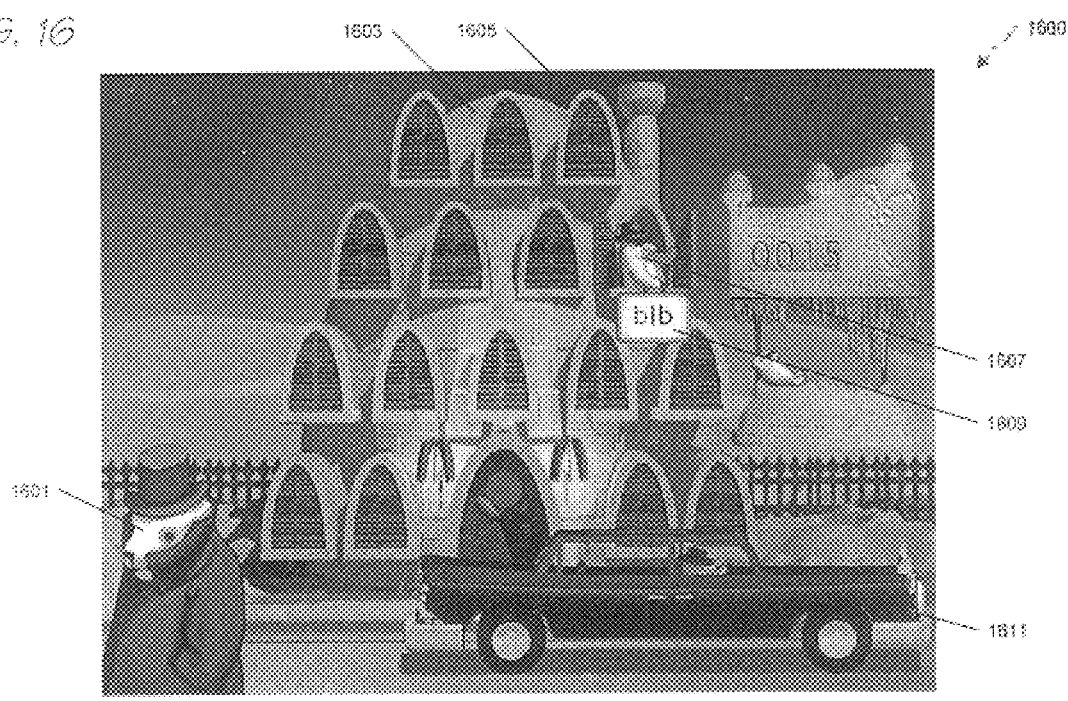

METHOD AND APPARATUS FOR TRAINING OF AUDITORY/VISUAL DISCRIMINATION USING TARGET AND DISTRACTOR PHONEMES/GRAPHICS

CROSS REFERENCE TO RELATED APPLICATIONS

This application is a Continuation-in-Part of U.S. patent application Ser. No. 08/982189, filed Dec. 17, 1997, now U.S. Pat. No. 5,927,988, entitled "METHOD AND APPARATUS FOR TRAINING OF SENSORY AND PERCEPTUAL SYSTEMS IN LLI SUBJECTS"; and is related to U.S. patent application Ser. No. 08/992071, filed Dec. 17, 1997, now U.S. Pat. No. 6,019,607, entitled "METHOD AND APPARATUS FOR TRAINING OF SENSORY AND PERCEPTUAL SYSTEMS IN LLI SUBJECTS"; and U.S. patent application Ser. No. 08/992072, filed Dec. 17, 1997 entitled "METHOD AND APPARATUS FOR TRAINING OF COGNITIVE AND MEMORY SYSTEMS IN HUMANS"; both assigned to Scientific Learning Corporation.

BACKGROUND OF THE INVENTION

1. Field of the Invention

This invention relates in general to the field of language education, and more specifically to a computer program for training a human's auditory processing system to discriminate between and accurately identify similarly sounding phonemes or words, and to associate representative graphemes with the phonemes or words.

2. Description of the Related Art

Up to ten percent of children have language-learning impairments (LLI) resulting from the inability to accurately process short duration acoustic events at the rates that occur in normal speech. Their trouble distinguishing among elements of speech is neurologically based and has far reaching consequences, including: academic failure, emotional and disciplinary problems, and possibly diminished lifelong achievement and self-image. No bracket of intelligence, race, gender or economic level is immune from this problem.

More specifically, Children with LLI have difficulty detecting and identifying sounds that occur simultaneously or in close proximity to each other—a phenomenon known as "masking." Because of masking, children with LLI require sounds that are as much as 45 decibels more intense than a preceding or subsequent masking noise to distinguish and understand them. In addition, children with LLI are consistently poorer at detecting a brief tone presented with a masking noise, particularly when the brief tone is turned on immediately prior to the masking noise. This phenomenon is called "backward masking." Similarly, when the brief tone is turned on immediately after the masking noise a similar decrease in detectability can occur. This phenomenon is called "forward masking". For a tone to be detected by a child with LLI in the presence of a masking noise, the tone must be separated in time or frequency from the masking noise.

The inability to accurately distinguish and process short duration sounds often causes children to fall behind in school. Since the children can't accurately interpret many language sounds, they can't remember which symbols represent which sounds. This deficiency causes difficulties in learning to read (translating from symbols to sounds), and in spelling. In fact, it is common for a child with LLI to fall two to three years behind his/her peers in speech, language and reading development.

One way children develop such auditory processing problems is from middle ear infections when they are young and beginning to develop the oral representations of language in the central auditory nervous system. When a child has an ear infection, fluid can build up and block or muffle the sound wave entering the ear causing intermittent hearing loss. Even if the infection doesn't permanently damage the ear, the child's brain doesn't learn to process some sounds because it hasn't heard them accurately before, on a consistent basis. This typically occurs during a critical period of brain development when the brain is building the nerve connections necessary to accurately process acoustic events associated with normal speech.

Researchers believe that the auditory processing problem is essentially one of timing. Vowel sounds like /a/ and /e/ usually last at least 100 milliseconds and typically have constant frequency content. Consonants, on the other hand, typically have modulated frequency components, and last less than 40 milliseconds. Children with LLI cannot process these faster speech elements, especially the hard consonants like /t/, /p/, /d/ and /b/, if they occur either immediately before or after vowels, or if they are located near other consonants. Rather than hearing the individual sounds that make up a particular phoneme, children with LLI integrate closely associated sounds together over time. Since the duration of vowels are typically longer than consonants, the modulated frequency portions of consonants are often lost in the integration, an affect that may also hinder the resolution of the vowel, particularly short duration vowels.

This problem of abnormal temporal integration of acoustic events over time is not limited to children with LLI. Rather, the problem extends to stroke victims who have lost the neurological connections necessary to process speech, as well as to individuals raised in one country, having one set of language phonemes, and attempting to learn the language of another country, having a distinct set of language phonemes. For example, it is known that an individual raised in Japan is not often presented with phonemes similar to the English r's and l's, because those consonants are not common in the Japanese language. Similarly, there are many subtleties in the sounds made by a speaker of Japanese that are difficult to distinguish unless raised in Japan. The phonetic differences between languages are distinctions that must be learned, and are often very difficult. But, they are clearly problems that relate to the temporal processing of short duration acoustic events.

The above described temporal processing deficiency has little if anything to do with intelligence. In fact, some LLI specialists argue that brains choosing this different route by which to absorb and reassemble bits of speech may actually stimulate creative intelligence, but at the expense of speech and reading problems.

Recent studies have shown that if the acoustic events associated with phonemes that are difficult to distinguish, such as /ba/ and /da/, are slowed down, or that the consonant portion of the phonemes are emphasized, that students diagnosed as LLI can accurately distinguish between the phonemes. In addition, if the interval between two complex sounds is lengthened, LLI students are better able to process the sounds distinctly.

Heretofore, the solution to the processing problem has been to place LLI students in extended special education and/or speech therapy training programs that focus on speech recognition and speech production. Or, more commonly, repetitive reading programs, phonic games, or other phonic programs are undertaken. These programs often last for years, with a success rate that is often more closely associated with the skill of the speech and language professional than with the program of study.

What is needed is a method and apparatus that allows a subject with abnormal temporal processing to train, or retrain their brain to recognize and distinguish short duration acoustic events that are common in speech. Moreover, what is needed is a program that repetitively trains a subject to distinguish phonemes at a normal rate, by emphasizing elements of speech to the point that they are distinguishable, or separating speech elements in time, and then adaptively adjusting the emphasis and separation of the speech elements to the level of normal speech. The adaptive adjustments should be made so as to encourage the subject to continue with the repetitions, and the number of repetitions should be sufficient to develop the necessary neurological connections for normal temporal processing of speech. Moreover, the program should provide acoustic signals to the brain that are better for phonetic training than normal human speech.

Furthermore, what is needed is a program that trains a subject to discriminate between similar phonemes in increasingly complex situations (i.e., identifying sounds at the beginning, middle and end of words), to identify sequences of stimuli that are delivered in rapid succession (i.e., at speeds common in normal speech), and to begin associating phonemes with particular graphic representations (graphemes).

SUMMARY

To address the above-detailed deficiencies, the present invention provides a method for adaptively developing neural activity, to improve signal differentiation in spoken language, the method utilizing speech processing for enhancing a subject's ability to distinguish between similar phonemes. The method includes: a) providing a plurality of stimulus sets, each of the stimulus sets having a target phoneme, and a plurality of distractor phonemes; b) presenting a processed target phoneme from one of the plurality of stimulus sets; c) creating a stimulus sequence, the stimulus sequence having the processed target phoneme from the one of the plurality of stimulus sets, within a plurality of distractor phonemes from the one of the plurality of stimulus sets; d) presenting the stimulus sequence to a subject; e) if the subject signals identification of the processed target phoneme, recording the identification as correct; f) repeating b)–e); and g) after a predetermined number of correct identifications, selecting an alternate stimulus set for presentation to the subject.

In another aspect, the present invention provides a method for adaptively training a subject to distinguish between similar sounds common in spoken language, the method applying emphasis to certain stop consonants within the similar sounds. The method includes: a) providing a plurality of processing levels to be applied to the similar sounds; b) providing a plurality of stimulus sets, each of the stimulus sets having a target sound, and a plurality of distractor sounds; c) creating a stimulus sequence, the stimulus sequence embedding a target sound, from within one of the plurality of stimulus sets, within a plurality of distractor sounds from the one of the plurality of stimulus sets; d) applying one of the plurality of processing levels to the sounds within the stimulus sequence; e) presenting the processed sounds of the stimulus sequence to a subject; and f) if the subject correctly identifies the target sound within the stimulus sequence a predetermined number of times, selecting a new stimulus set from the plurality of stimulus sets, and repeating c)–e).

In yet a further aspect, the present invention provides a method for training a subject to associate processed phonemes with their corresponding graphemes. The method includes: a) providing a plurality of stimulus sets, each of the stimulus sets having a target phoneme and a plurality of distractor phonemes, the target and distractor phonemes having corresponding graphemes; b) aurally presenting a processed target phoneme from one of the plurality of stimulus sets; c) creating a stimulus sequence having the processed target phoneme embedded within a plurality of associated distractor phonemes; d) presenting graphemes associated with the phonemes within the stimulus sequence to a subject; e) if the subject signals identification of a grapheme corresponding to the processed target phoneme, recording the identification as correct; and f) repeating b)–e) for each of the plurality of stimulus sets.

BRIEF DESCRIPTION OF THE DRAWINGS

These and other objects, features, and advantages of the present invention will become better understood with regard to the following description, and accompanying drawings where:

FIG. 16 is a pictorial representation of a screen in Polar Cop illustrating a Reward Play.

DETAILED DESCRIPTION

Figure 1:
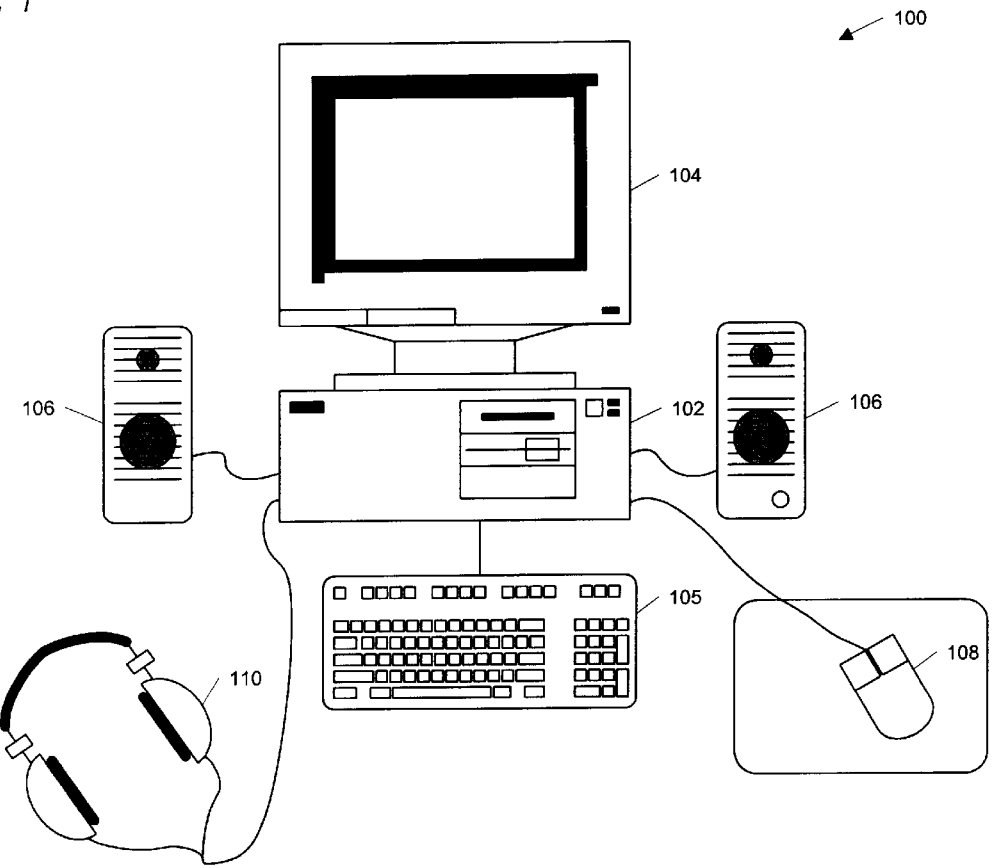
FIG. 1 is a block diagram of a computer system for executing a program according to the present invention.

Referring to FIG. 1, a computer system 100 is shown for executing a computer program to train, or retrain a subject, according to the present invention. The computer system 100 contains a computer 102, having a CPU, memory, hard disk and CD ROM drive (not shown), attached to a monitor 104. The monitor 104 provides visual prompting and feedback to the subject during execution of the computer program. Attached to the computer 102 are a keyboard 105, speakers 106, a mouse 108, and headphones 110. The speakers 106 and the headphones 110 provide auditory prompting and feedback to the subject during execution of the computer program. The mouse 108 allows the subject to navigate through the computer program, and to select particular responses after visual or auditory prompting by the computer program. The keyboard 105 allows an instructor to enter alpha numeric information about the subject into the computer 102. Although a number of different computer platforms are applicable to the present invention, embodiments of the present invention execute on either IBM compatible computers or Macintosh computers.

Figure 2:
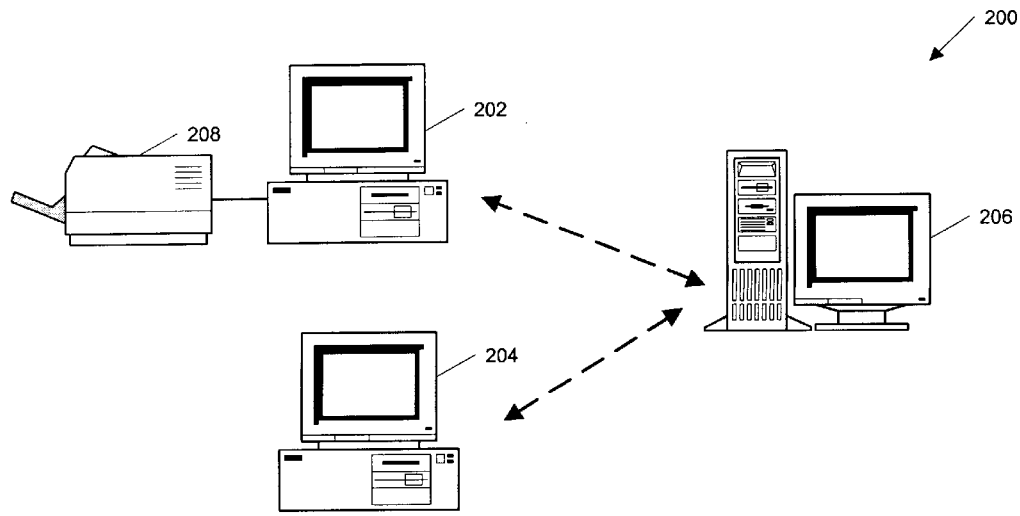
FIG. 2 is a block diagram of a computer network for executing a program according to the present invention.

Now referring to FIG. 2, a computer network 200 is shown. The computer network 200 contains computers 202, 204, similar to that described above with reference to FIG. 1, connected to a server 206. The connection between the computers 202, 204 and the server 206 can be made via a local area network (LAN), a wide area network (WAN), or via modem connections, directly or through the Internet. A printer 208 is shown connected to the computer 202 to illustrate that a subject can print out reports associated with the computer program of the present invention. The computer network 200 allows information such as test scores, game statistics, and other subject information to flow from a subject's computer 202, 204 to a server 206. An administrator can then review the information and can then download configuration and control information pertaining to a particular subject, back to the subject's computer 202, 204.

Before providing a detailed description of the present invention, a brief overview of certain components of speech will be provided, along with an explanation of how these components are processed by LLI subjects. Following the overview, general information on speech processing will be provided so that the reader will better appreciate the novel aspects of the present invention.

Figure 3:
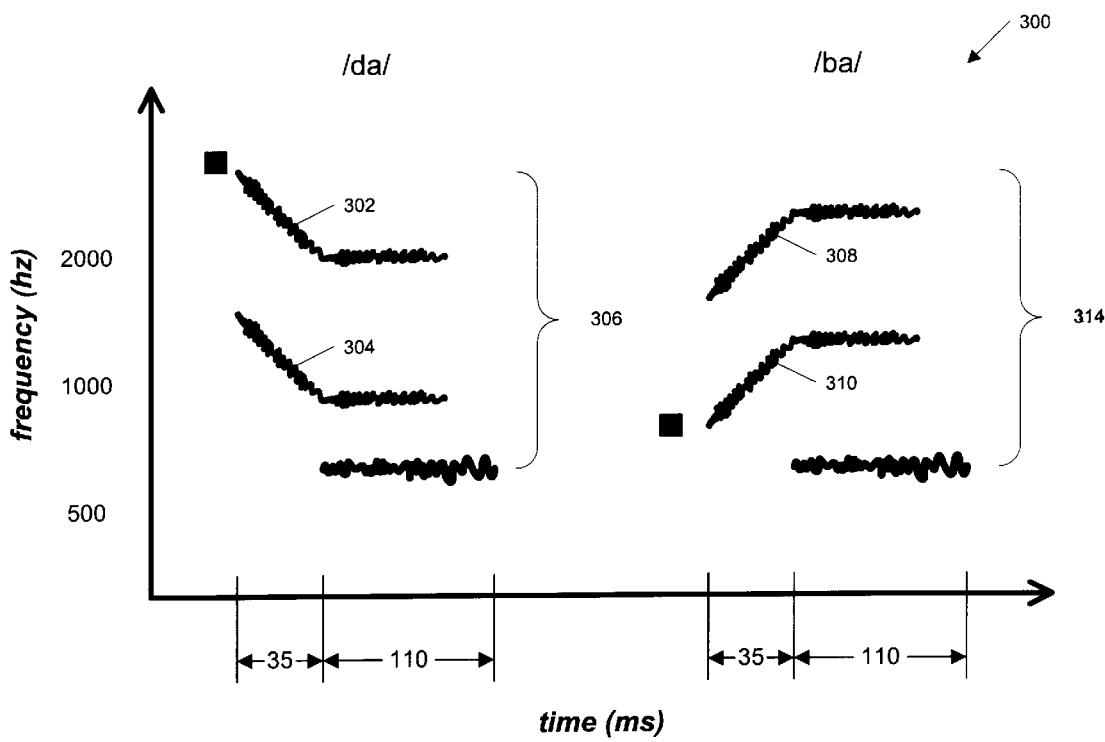
FIG. 3 is a chart illustrating frequency/energy characteristics of two phonemes within the English language.

Referring to FIG. 3, a chart is shown that illustrates frequency components, over time, for two distinct phonemes within the English language. Although different phoneme combinations are applicable to illustrate features of the present invention, the phonemes /da/ and /ba/ are shown. For the phoneme /da/, a downward sweep frequency component 302, at approximately 2.5–2 khz is shown to occur over a 35 ms interval. In addition, a downward sweep frequency component 304, at approximately 1 khz is shown to occur during the same 35 ms interval. At the end of the 35 ms interval, constant frequency components 306 are shown, whose duration is approximately 110 ms. Thus, in producing the phoneme /da/, the stop consonant portion of the element /d/ is generated, having high frequency sweeps of short duration, followed by a long vowel element /a/ of constant frequency.

Also shown are frequency components for a phoneme /ba/. This phoneme contains an upward sweep frequency component 308, at approximately 2 khz, having a duration of approximately 35 ms. The phoneme also contains an upward sweep frequency component 310, at approximately 1 khz, during the same 35 ms period. Following the stop consonant portion /b/ of the phoneme, are constant frequency vowel portions 314 whose duration is approximately 110 ms.

Thus, both the /ba/ and /da/ phonemes begin with stop consonants having modulated frequency components of relatively short duration, followed by a constant frequency vowel components of longer duration. The distinction between the phonemes exists primarily in the 2 khz sweeps during the initial 35 ms interval. Similarity exists between other stop consonants such as /ta/, /pa/, /ka/ and /ga/.

Figure 4:
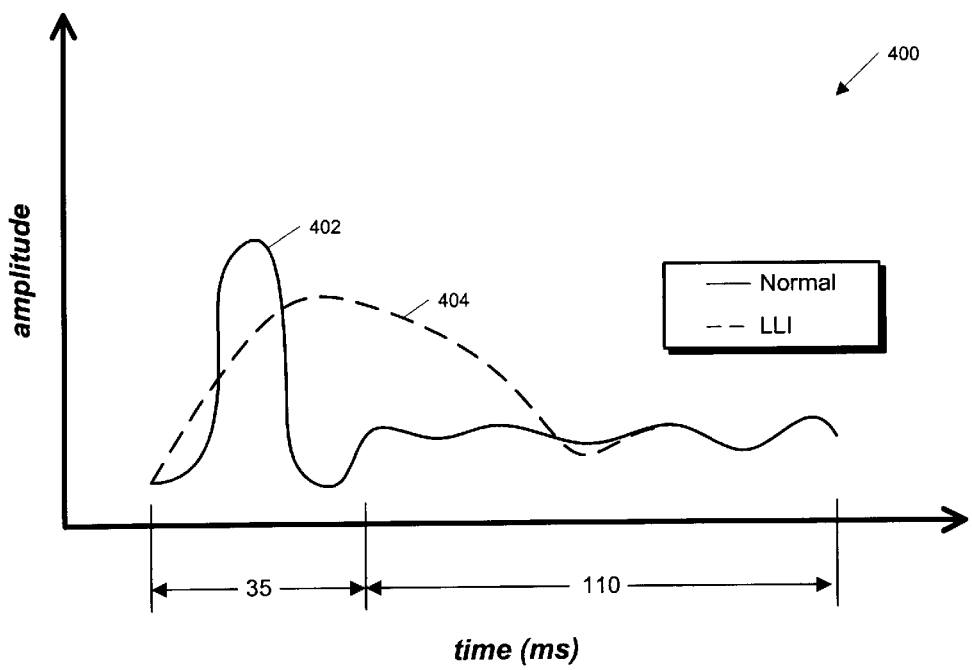
FIG. 4 is a chart illustrating auditory reception of a phoneme by a subject having normal receptive characteristics, and by a subject whose receptive processing is impaired.

Referring now to FIG. 4, the amplitude of a phoneme, for example /ba/, is viewed in the time domain. A short duration high amplitude peak waveform 402 is created upon release of either the lips or the tongue when speaking the consonant portion of the phoneme, that rapidly declines to a constant amplitude signal of longer duration. For an individual with normal temporal processing, the waveform 402 will be understood and processed essentially as it is. However, for an individual who is learning-language impaired, or who has abnormal temporal processing, the short duration, higher frequency consonant burst will be integrated over time with the lower frequency vowel, and depending on the degree of impairment, will be heard as the waveform 404. The result is that the information contained in the higher frequency sweeps associated with consonant differences, will be muddled, or indistinguishable.

With the above general background of speech elements, and how LLI subjects process them, a general overview of speech processing will now be provided. As mentioned above, one problem that exists in LLI subjects is the inability to distinguish between short duration acoustic events. If the duration of these acoustic events is stretched, in the time domain, it is possible to train LLI subjects to distinguish between these acoustic events. An example of such time domain stretching is shown in FIG. 5, to which attention is now directed.

Figure 5:
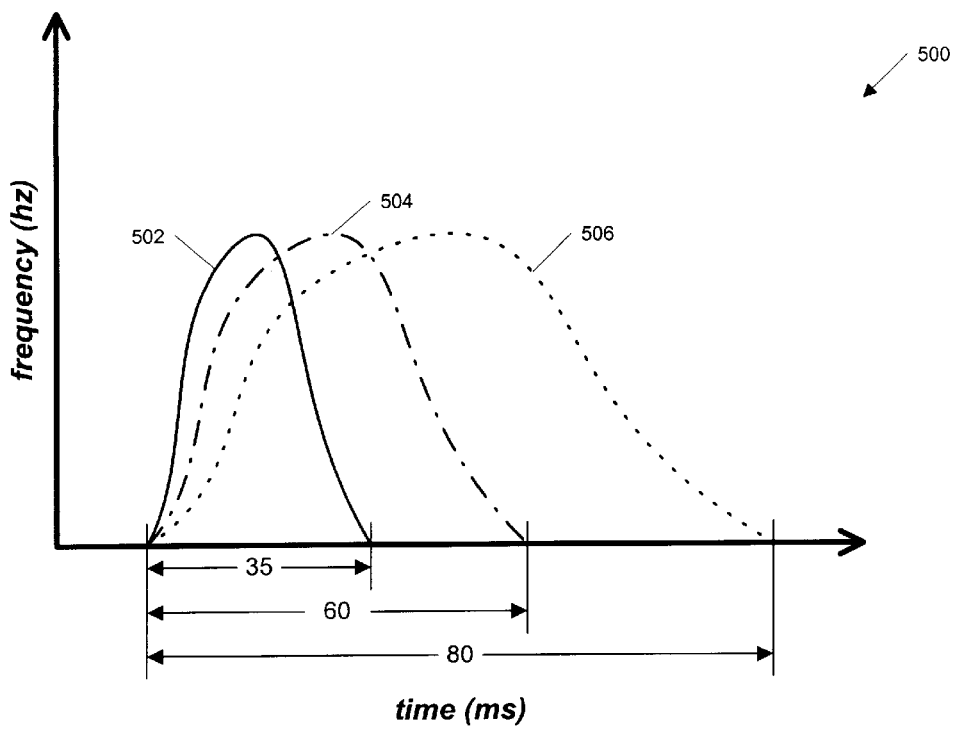
FIG. 5 is a chart illustrating stretching of a frequency envelope in time, according to the present invention.

In FIG. 5, a frequency vs. time graph 500 is shown that illustrates a waveform 502 having short duration characteristics similar to the waveform 402 described above. Using existing computer technology, the analog waveform 502 can be sampled and converted into digital values. The values can then be manipulated so as to stretch the waveform in the time domain to a predetermined length, while preserving the amplitude and frequency components of the modified waveform. The modified waveform can then be converted back into an analog waveform for reproduction by a computer, or by some other audio device. The waveform 502 is shown stretched in the time domain to durations of 60 ms (waveform 504), and 80 ms (waveform 506). By stretching the consonant portion of the waveform 502 without effecting its frequency components, subjects with LLI can begin to hear distinctions in common phonemes.

Figure 6:
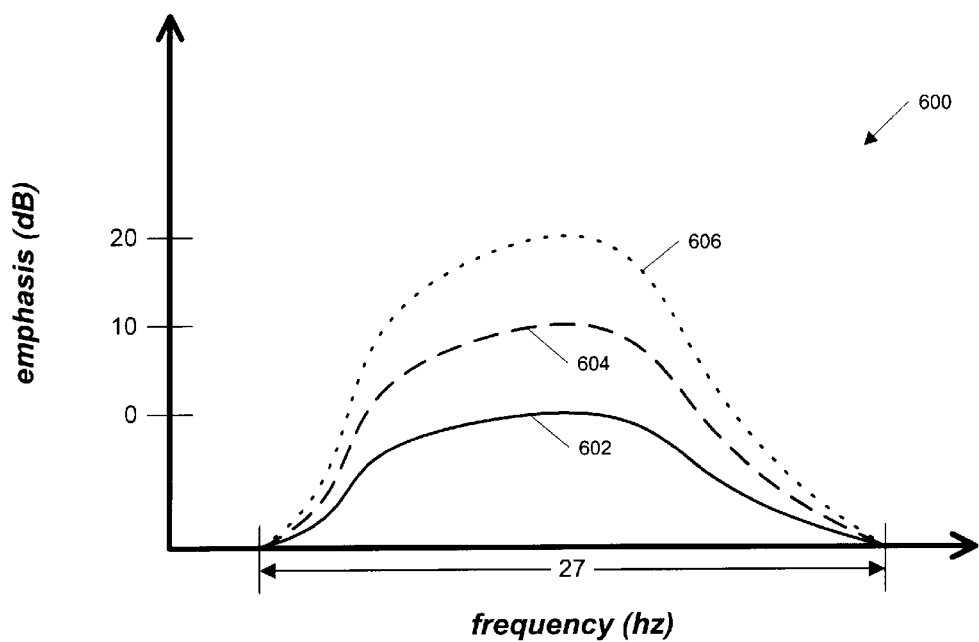
FIG. 6 is a chart illustrating emphasis of selected frequency components, according to the present invention.

Another method that may be used to help LLI subjects distinguish between phonemes is to emphasize selected frequency envelopes within a phoneme. Referring to FIG. 6, a graph 600 is shown illustrating a frequency envelope 602 whose envelope varies by approximately 27 hz. By detecting frequency modulated envelopes that vary from say 3–30 hz, similar to frequency variations in the consonant portion of phonemes, and selectively emphasizing those envelopes, they are made more easily detectable by LLI subjects. A 10 dB emphasis of the envelope 602 is shown in waveform 604, and a 20 dB emphasis in the waveform 606.

Figure 7:
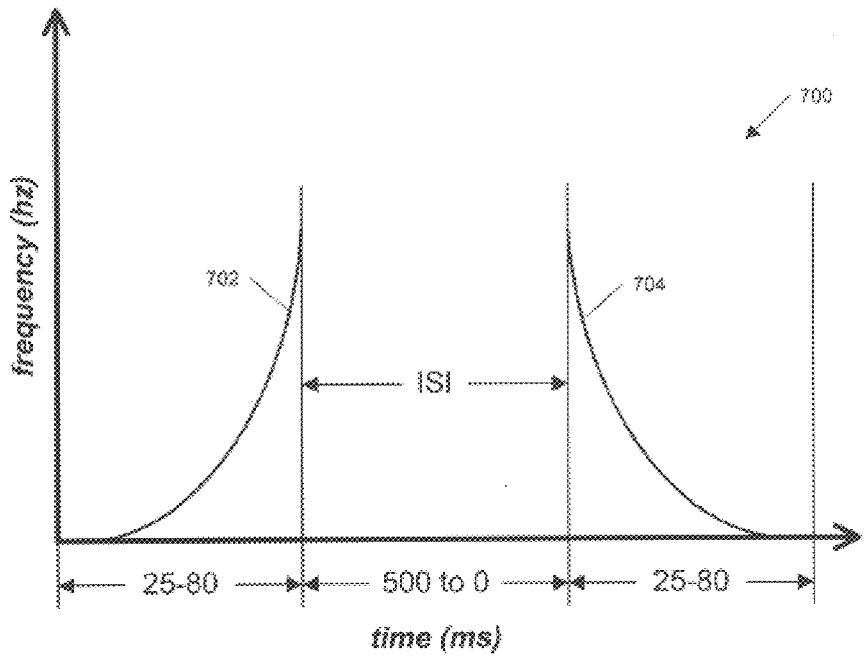
FIG. 7 is a chart illustrating up-down frequency sweeps of varying duration, separated by a selectable inter-stimulus-interval (ISI), according to the present invention.

A third method that may be used to train LLI subjects to distinguish short duration acoustic events is to provide frequency sweeps of varying duration, separated by a predetermined interval, as shown in FIG. 7. More specifically, an upward frequency sweep 702, and a downward frequency sweep 704 are shown, having duration's varying between 25 and 80 milliseconds, and separated by an inter-stimulus interval (ISI) of between 500 and 0 milliseconds. The duration and frequency of the sweeps, and the inter-stimulus interval between the sweeps are varied depending on the processing level of the LLI subject, as will be further described below.

Utilization of up-down frequency sweeps with varying ISI has been fully described in U.S. patent application Ser. No. 08/858,961, filed May 20, 1997, entitled "METHOD AND DEVICE FOR ENHANCING THE RECOGNITION OF SPEECH AMONG SPEECH-IMPAIRED INDIVIDUALS", now U.S. Pat. No. 5,813,862, and is hereby incorporated by reference.

The above described methods have been combined in a unique fashion by the present invention to provide an adaptive training method and apparatus for training subjects having abnormal temporal processing abilities to recognize and distinguish short duration acoustic events that are common in speech. More specifically, emphasis has been used to intensify format transitions of stop consonants that are presented to a subject. It is believed that the differential gain of critical acoustic components generates more vigorous neural activity, which leads to better signal differentiation by neural networks involved in speech perception.

The present invention is embodied into a computer program entitled Fast ForWord II by Scientific Learning Corporation. The computer program is provided to an LLI subject via a CD-ROM that is input into a general purpose computer such as that described above with reference to FIG. 1. In addition, a user may log onto a server, via an Internet connection, for example, to upload test results, and to download training parameters for future exercises. Specifics of the present invention will now be described with reference to FIGS. 8–16.

Figure 8:
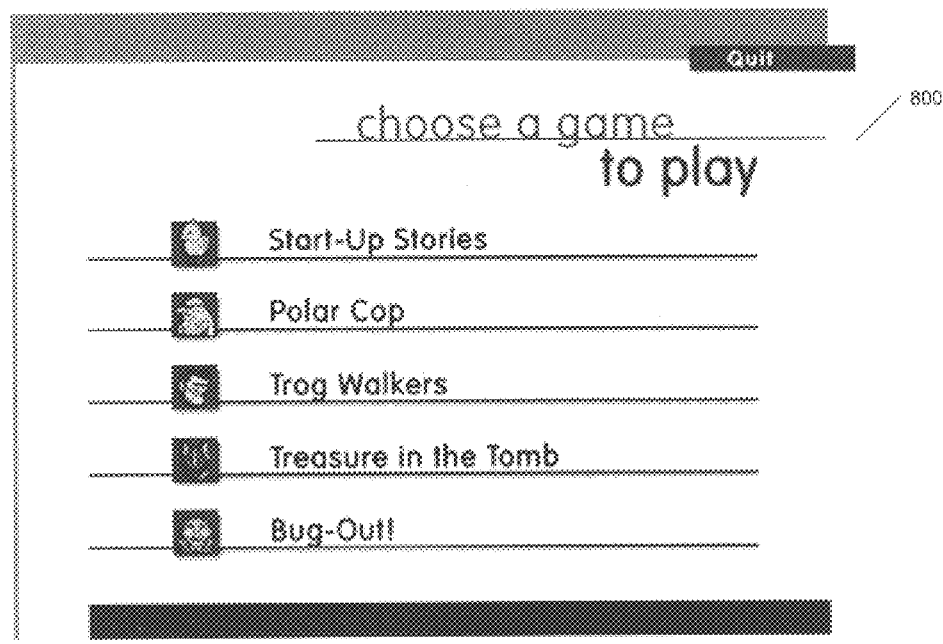
FIG. 8 is a pictorial representation of a game selection screen according to the present invention.

Referring first to FIG. 8, a pictorial representation is shown of a game selection screen 800. The game selection screen 800 is similar to that provided to a subject upon initialization of the computer program according to the present invention. The game selection screen 800 includes the titles of five computer games that provide distinct training exercises for improving language recognition in subjects who abnormally process temporal acoustic events, and for building, or rebuilding the neurological connections necessary to accurately process phonemes at the rates common in speech. The game titles include: 1) Start-Up Stories; 2) Polar Cop; 3) Trog Walkers; 4) Treasure in the Tomb; and 5) Bug-Out!.

When a subject begins execution of the Fast ForWord II computer program, he/she is presented with a screen similar to the screen 800. More specifically, upon initiation of the program, the subject is presented with a screen that lists the subjects that are currently being trained by the program. The subject, or instructor, then selects his/her name from the list. Once the subject has selected his/her name, a screen similar to 800 appears, typically listing the five programs, according to a training schedule that is dictated by the program, or is modified by an instructor. The order of the games that is presented in the screen 800 may vary from day to day, depending on which games the subject has previously played. In addition, after a subject has completed play of a particular game, that game may be shown "grayed out", indicating that it may not be selected again that day unless all other scheduled exercises have already been played. The subject then selects to play one of the games listed.

In one embodiment, a training schedule is provided by a certified Speech and Language Professional (SLP), and the SLP oversees each training session according to the schedule. An exemplary schedule requires a subject to cycle through the games for an hour and forty minutes, five days per week, for approximately six weeks.

In an alternative embodiment, the game schedule is specified by an SLP at a remote server, and the daily parameters of the schedule are downloaded to the subject's computer, either daily or weekly. The schedule can be optimized over the course of the training program according to the performance or skill of the subject. It can also be used to help manage time in each game so that all of the games are completed in about the same time at the end of the training program. This can be accomplished by an automated computer algorithm that adjusts the time allotted for each training exercise. This algorithm is individually adaptive and can adjust the times for each exercise on an individual subject basis using performance and estimates of time to complete the entire training sequence. This embodiment allows a subject to obtain the benefits of the Fast ForWord II program, and the oversight of a certified SLP, regardless of his/her geographic location. One skilled in the art will appreciate that the training schedule could either be provided in a window on the subject's computer, or could actually control the game selection screen to prompt the user only for those games required on a particular day.

Once a subject selects a particular game, he/she is taken into that particular game's module. Alternatively, once the subject selects his/her name from the list, the particular games may be presented, in a predefined order, without requiring the subject to first select the game.

The present application provides a detailed description of the game "Polar Cop". The other games shown in FIG. 8 are described in co-pending U.S. Patent Applications: SLC: 811 (Trog Walkers); SLC: 812 (Treasure in the Tomb); SLC: 813 (Bug Out!); and SLC: 814 (Start-Up Stories), which are hereby incorporated by reference.

Polar Cop is a game that adaptively trains a subject to distinguish between similarly sounding phonemes and to associate phonemes with their graphemes. The game presents a series of trials that provide target phonemes of processed speech to the subject for identification. As the subject accurately identifies the target phonemes within a stream of distractor phonemes, the amount of processing applied to the phonemes is reduced, ultimately to the level of normal speech. The trials are placed within a game environment to entertain and amuse the subject so that multiple iterations are considered enjoyable rather than tedious. For purposes of the present invention, the terms "phoneme" and "word" are used interchangeably, to designate particular aural events that must be perceived by a subject.

The premise of the Polar Cop game is that a ring of evil, sociopathic penguins, known as the Word Burglars, has stolen valuable words. The subject being tested is a young investigator that has been provided with a special word locating zoom camera that is used to spot the stolen words. The subject helps the polar cops jail the evil penguins with the evidence obtained in the photos, and the subject's growing knowledge of the letters.

A complete description of the trial methodology used by Polar Cop, as well as the phonemes tested, and the adaptive nature of the game, will be provided below with reference to FIG. 15. However, to better appreciate the methodology used within Polar Cop, an overview of the game will first be provided, with reference to several screens within the game.

Figure 9:
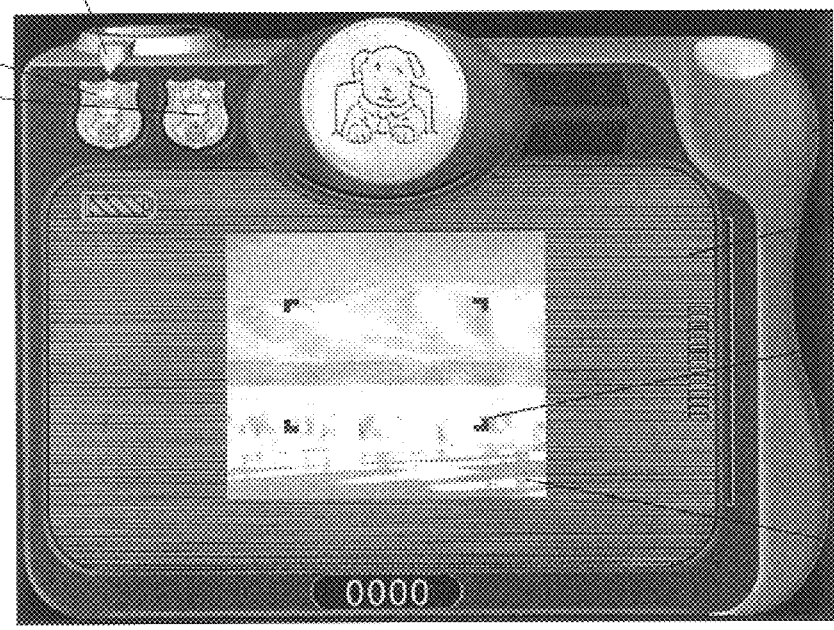
FIG. 9 is a pictorial representation of an initial game screen for a game entitled "Polar Cop" according to the present invention.

Referring to FIG. 9, a screen 900 is shown that contains a special word locating camera 902. A subject is provided a view window 904 from the back of the camera 902 to view a snowy landscape. Centered in the view window 904 is a center frame 906, and target or frame markings 908. The target markings 908 are highlighted when the subject can take a snapshot of a potential word burglar. In the upper left corner of the camera 902 is a phase indicator 912 for indicating to the subject whether the trials he/she is currently performing are within phase I, indicated by pointing to badge 910, or phase II, indicated by pointing to badge 911. At the bottom of the scene 900 is a score indicator 914 for providing the subject with feedback of his/her success.

Figure 10:
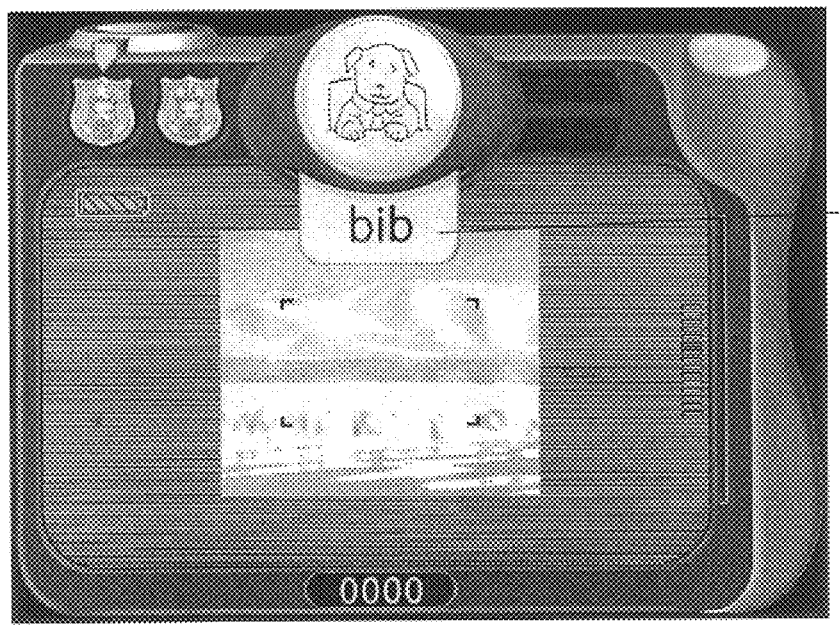
FIG. 10 is a pictorial representation of a game screen in Polar Cop illustrating initiation of a trial for the phoneme "bib".

Referring now to FIG. 10, a screen 1000 is shown that includes all of the elements listed in FIG. 9. In addition, a grapheme 1020 is provided, illustrating a particular phoneme to be tested. The grapheme is presented to the subject when the subject initiates a trial. In one embodiment of the present invention, the subject initiates a trial by pressing a button on a computer mouse, such as the one described above with reference to FIG. 1. When the subject initiates a trial, the grapheme 1020 is presented. Within the grapheme 1020, the particular consonant that is being tested is highlighted in a color different from the other letters in the phoneme. For example, in the scene 1000, the first letter "b" is shown in a color different from the letters "ib". This provides a visual clue to the subject regarding what he/she will be tested on in the trial.

Coincident with presentation of the grapheme 1020, an aural presentation of the phoneme represented by the grapheme 1020 is played for the subject. The aural presentation will be played on speakers or headphones attached to a computer, similar to those shown above in FIG. 1. The aural presentation of the phoneme may be processed to enhance the subject's ability to distinguish it from other similarly sounding phonemes, as will be further described below.

Figure 11:
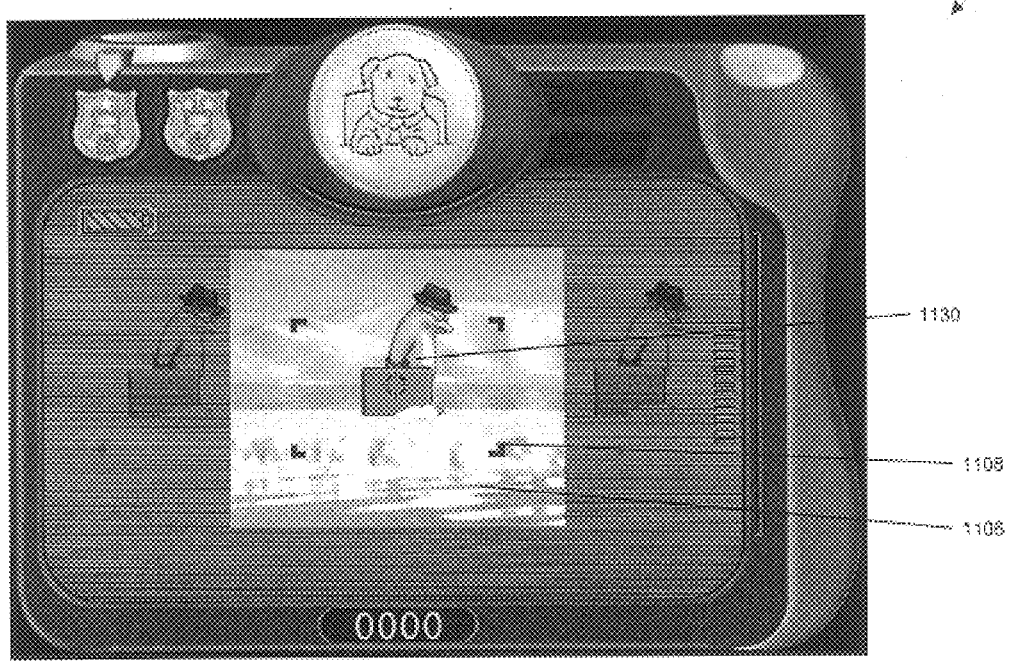
FIG. 11 is a pictorial representation of a game screen in Polar Cop illustrating progression of a stimulus sequence created to train a subject to distinguish between a target phoneme and a distractor phoneme.

Referring now to FIG. 11, a screen 1100 is shown. The screen 1100 includes all of the elements described above in FIG. 9. It should be appreciated that the grapheme 1020 is no longer shown within the screen 1100. Thus, after the subject initiates a trial, and is presented with the grapheme 1020, and its associated aural presentation, the grapheme 1020 is removed. At this point, a series of characters 1130 proceed right to left through the center view 1106. In one embodiment, the characters include penguins dressed in a variety of suspicious outfits. In alternative scenes, the characters proceeding thru the center screen 1106 include fishes, toasters, televisions, and safes.

As the characters 1130 proceed thru the center view 1106, they momentarily pause to allow the subject to take their picture. The pause is graphically enhanced by changing the color of the target marks 1108. In one embodiment, the target marks 1108 change from black to red while the character 1130 is within the center view 1106. In addition, as each character 1130 proceeds thru the center view 1106, a phoneme is presented aurally to the subject. In one embodiment, the phoneme is of two types: 1) a target phoneme; or 2) a distracter phoneme. The target phoneme is the phoneme that was presented to the subject upon initiation of the trial. The distracter phoneme is a phoneme that sounds similar to target phoneme. So, as the characters 1130 proceed thru the center view 1106, either a distractor phoneme or a target phoneme is aurally presented. The subject's task in the trial is to snap a picture when he/she is presented with the target phoneme. In one embodiment, the picture may be snapped by pressing a mouse button when the target marks 1108 change color.

Figure 12:
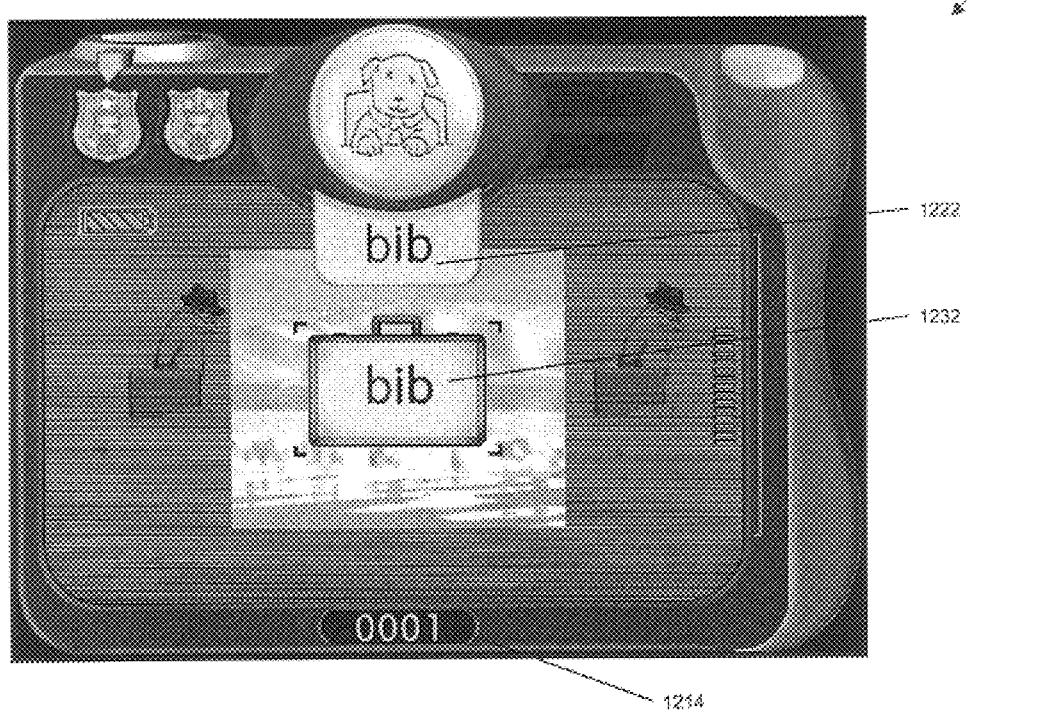
FIG. 12 is a pictorial representation of a game screen in Polar Cop illustrating correct identification of the phoneme "bib" from within a stimulus sequence.

Referring now to FIG. 12, if the subject correctly discerns when the target phoneme is played, and snaps a picture of the character 1130, the target phoneme is presented to the subject as shown by the briefcase 1232. In addition, the original grapheme 1222 representative of the phoneme embedded in the target word is presented. This indicates to the subject that he/she has correctly identified the phoneme, and enhances their association of the aurally played phoneme with its grapheme. In addition, the subject's score 1214 is incremented. If the subject incorrectly selects one of the distracter phonemes as the target phoneme, or allows the target phoneme to pass thru the center view 1106 without being selected, a bell (or "thunk") is played, alerting the subject that they have failed to accurately detect the target phoneme. After a trial is either passed, or failed, the game screen 900 is presented to allow the subject to initiate another trial.

With the above overview of the Polar Cop game, a detailed description of the methodology, and adaptive controls of the game will now be provided.

STIMULUS SETS

In one embodiment, Polar Cop provides trials to train a subject to distinguish between the consonants—b, d, g, p, t, k, c, ck, sh, and st, using ordered sets called "stimulus sets". Each stimulus set provides a target word, such as "bib", and three distractor words, such as "sib, fib, and rib". In this example, the stimulus set uses consonant-vowel-consonant (CVC) words to train the subject to recognize the initial consonant "b" of the target word "bib". Other stimulus sets are provided to test consonant discrimination in combination with other vowels, consonant discrimination at the end of words, and consonant discrimination in consonant-vowel-consonant-consonant (CVCC) words. A complete list of the stimulus sets used in Polar Cop are provided in Appendix A.

STIMULUS STREAMS

As mentioned above with reference to FIG. 11, upon initiation of a trial, a sequence of characters 1130 proceed through the center view 1106 of the camera. As the characters 1130 proceed through the center view, they pause while a word is aurally presented. The word that is presented is either a target word, such as "bib", or a distractor word, such as "sib", depending on the trial. The words that are presented, and their order of presentation, are dependent on the stimulus set selected for the trial. Thus, from a given stimulus set, a stimulus stream is constructed for presentation to the subject.

In one embodiment, the rules for constructing a stimulus stream are as follows: 1) A stimulus stream consists of 5 to 8 items (3 to 5 in Training mode); 2) any item except the first one can be the target word; 3) the target word can occur only one time within a stimulus stream; and 4) initially, a single distractor word is used, building up to as many as three distractor words, depending on a subject's progress. For example, if a subject initiates a trial, and the target word is "bib", a stimulus stream might be created that looks like: "sib, sib, sib, sib, bib, sib". The placement of the target word within the stimulus stream, and the number of times the distractor word is presented prior to the target word, is random for each trial. After construction of the stimulus stream, the words are presented, along with an associated character 1130, as it passes through the center view 1106.

SPEECH PROCESSING

For each trial presented to a subject, the words within the stimulus stream may be processed to enhance the subject's ability to distinguish the target word from the distractor words. In one embodiment, Polar Cop provides 3 levels of speech processing for the target consonant portion of the target and distractor words. Level 1 provides 20 dB of emphasis, without any time domain expansion. Level 2 provides 10 dB of emphasis, without any time domain expansion. Level 3 provides 0 dB of emphasis, without any time domain expansion (i.e., normal speech).

The emphasis uses an algorithm that differentially amplifies and disambiguates faster phonetic elements in speech. "Fast elements" in speech are defined as those that occur in the 3–30 Hz range within an envelope of narrow-band speech channels of a rate changed speech signal. An emphasis algorithm for these fast elements was implemented using two methods: a filter-bank summation method and an overlap-add method based on a short-time Fourier transform. Both of these emphasis algorithms, as well as other speech processing methods are fully described in co-pending U.S. patent application Ser. No. 08/982189 (Docket SLC: 707A), filed Dec. 17, 1997, entitled "METHOD AND APPARATUS FOR TRAINING OF SENSORY AND PERCEPTUAL SYSTEMS IN LLI SUBJECTS".

HIT WINDOW

As the stimulus stream is presented to a subject, and as the characters 1130 proceed thru the center view 1106 of the camera, the subject is given a limited time within which he/she must signal a selection. This limited time is referred to as the "hit window". The hit window begins after a word sound is done playing, and extends for a period of time prior to the next word in the stimulus stream beginning. In one embodiment, a hit window of 1000 ms (1 second) has been chosen, although the hit window can easily be modified if alternate times prove beneficial. If the subject does not signal a selection of the target word within the hit window, the subject will have failed the trial.

DISPLAY PHASES

Within the Polar Cop game, there are two types of display modes, known as "Display Phases" in the game play. Phase I is similar to that described above with reference to FIG'S 9–12. In Phase I, upon initiation of a trial, a subject is presented with an auditory target word, and with its visual grapheme. The target word is played and the visual grapheme is presented briefly. Choices then proceed thru the center view of the camera, with auditory distractor and target words presented. When in Phase I, no graphemes are provided as the distractor and target words are played. Upon correct selection of the target word, its associated grapheme is shown.

Figure 13:
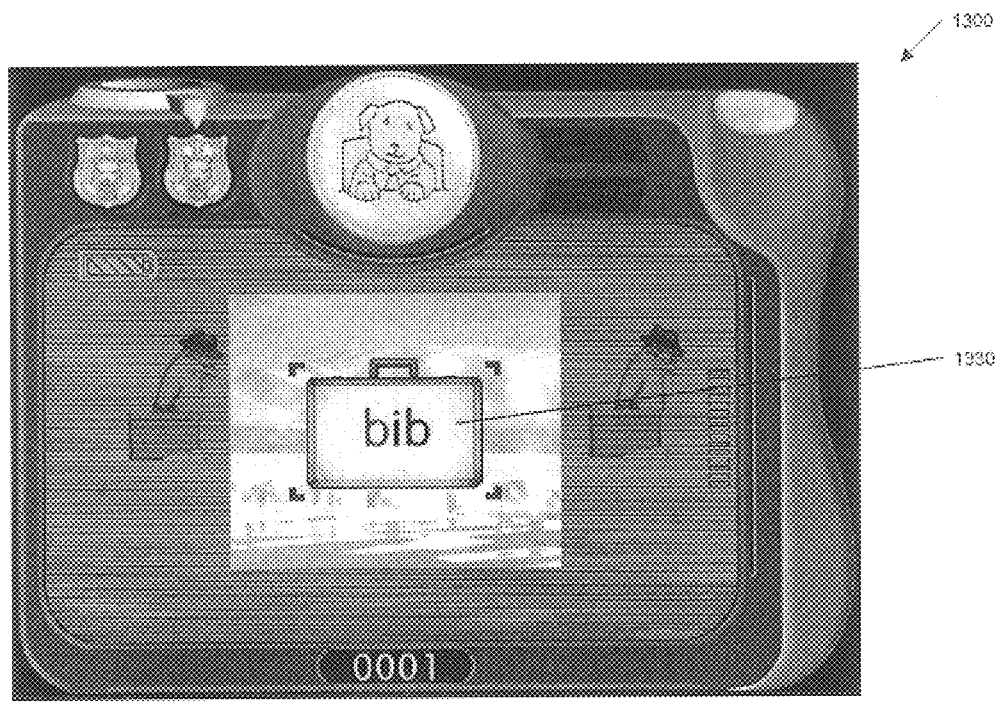
FIG. 13 is a pictorial representation of a game screen in Polar Cop illustrating progression of a stimulus sequence that provides a grapheme for both target and distractor phonemes.

Referring to FIG. 13, a screen 1300 is shown for game play in Phase II. In Phase II, when a subject initiates a trial, the target word is presented aurally only. No corresponding visual grapheme is presented. As the trial begins, and the characters proceed thru the center view, the characters turn into an associated grapheme 1330, corresponding to their distractor or target word, and their word is played. This provides the subject with both visual and auditory cues of the word being presented, to assist the subject not only in distinguishing between words aurally, but also distinguishing between them visually. In addition, Phase II trains the subject to visually associate particular graphemes with their associated aurally presented words.

Figure 14:
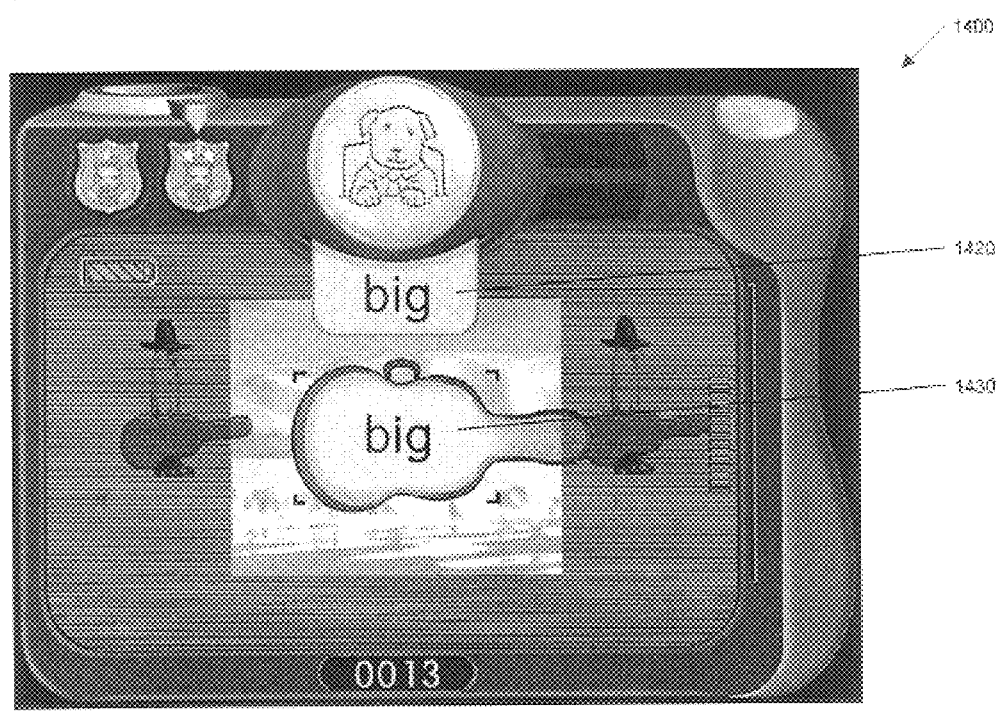
FIG. 14 is a pictorial representation of a game screen in Polar Cop illustrating correct identification of the phoneme "big" from within the stimulus sequence shown in FIG. 13.

Referring to FIG. 14, a screen 1400 is shown when a subject correctly selects the target word. In this instance, a visual cue 1420 is presented, along with a grapheme 1430, to indicate to the subject that he/she has properly identified the target word and/or its associated grapheme.

Figure 15A:
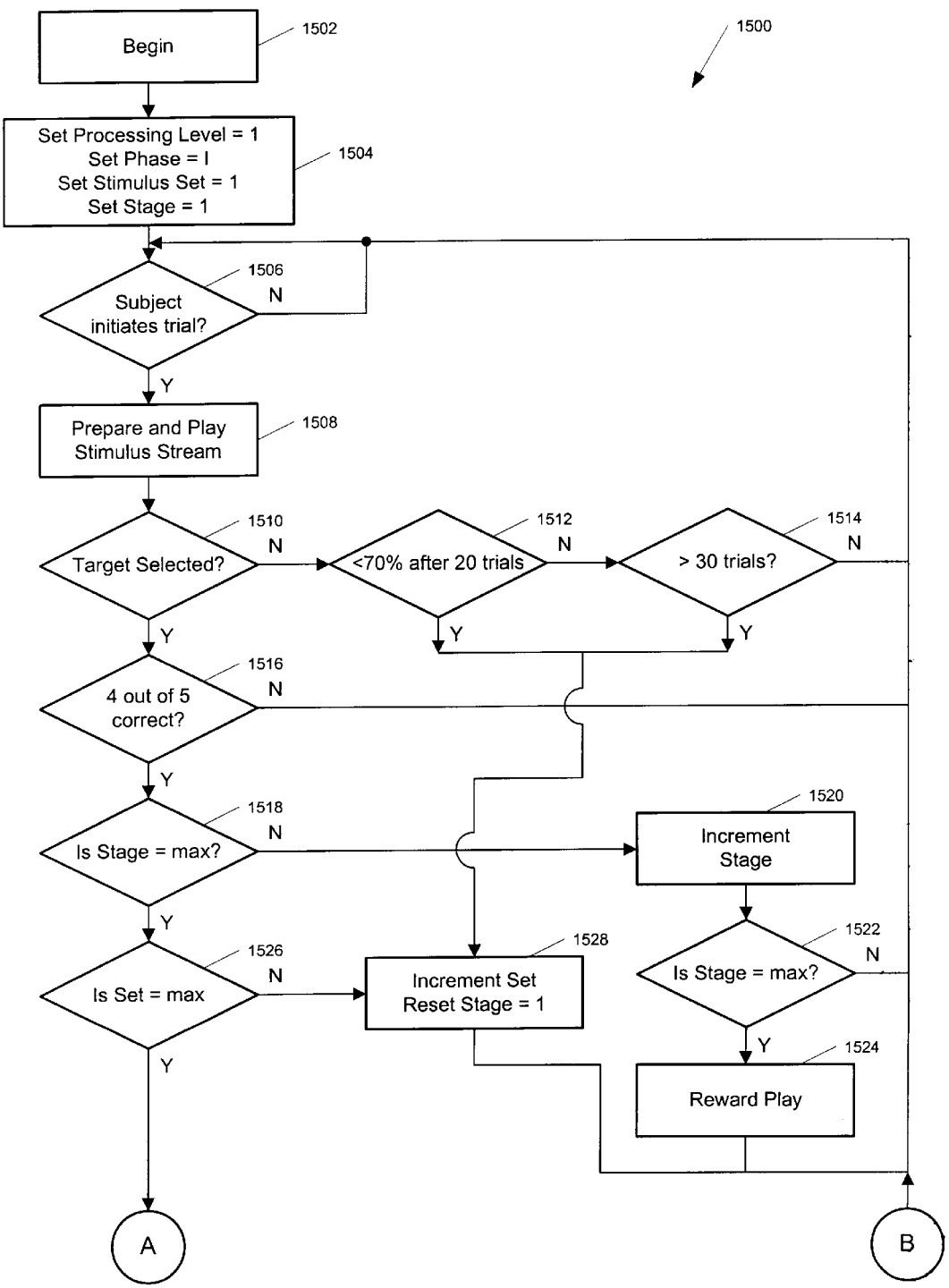
FIG. 15 is a flow chart illustrating the adaptive auditory training procedures embodied in the game Polar Cop.
Figure 15B:
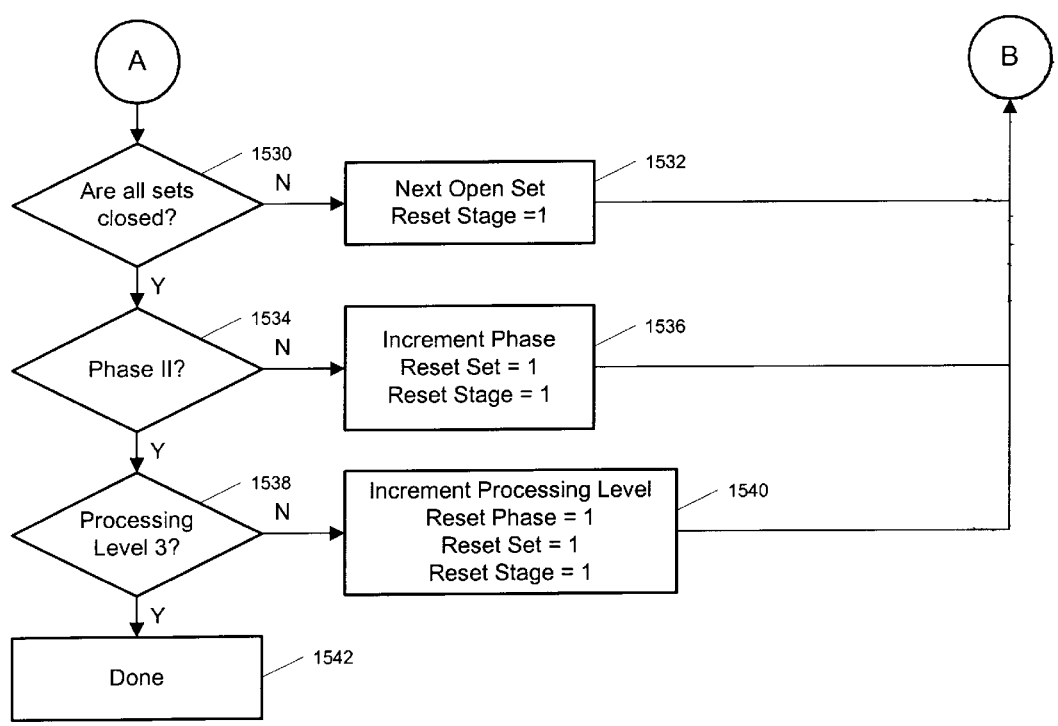

Having provided a description of the stimulus sets used for training, of the methodology used to create stimulus streams, of the various skill levels associated with processing the stimulus streams, and the different phases of game play, a flow chart, as represented in FIG. 15, will now be described that illustrates the adaptive sequencing of Polar Cop thru all the sets, levels and phases.

Referring to FIG. 15, a flow chart 1500 is shown illustrating the adaptive training methodology incorporated in the game Polar Cop. Game play begins at block 1502 and proceeds to block 1504.

At block 1504, the processing level is set to 1, the phase is set to 1, the stimulus set is set to 1 and the stage is set to 1. Recall that in one embodiment of the present invention, there are 3 processing levels for stimulus streams. Processing level 1 refers to providing 20 dB of emphasis for the target and distractor words. Phase I refers to game play that provides both an aural prompt and an associated grapheme to a subject upon initiation of a trial. Stimulus set 1 refers to the first stimulus set, within the 62 stimulus sets shown in Appendix A.

For each stimulus set, at each processing level, within each phase, there are 4 stages that must be passed by a subject. Each stage refers to a particular set of target/distractor combinations. For example, using stimulus set 1, the target word is "bib" and the distractor words are "sib, fib, and rib". Stage 1 refers to a set of trials that randomly sequences the target word "bib" within a sequence of distractor words "sib". Stage 2 refers to a set of trials that randomly sequences the target word "bib" within a sequence of distractor words "fib". Stage 3 refers to a set of trials that randomly sequences the target word "bib" within a sequence of distractor words "rib". Stage 4 refers to a set of trials that randomly sequences the target word "bib" within a random sequence of distractor words including "sib, fib, and rib". Once the processing level, phase, stimulus set, and stage have been initialized, flow proceeds to decision block 1506.

At decision block 1506 a determination is made as to whether the subject has initiated a trial. Recall from the discussion above with respect to FIG. 9, a subject initiates a trial by pushing a button on a mouse. Until the subject initiates a trial, the game remains at decision block 1506. Once the subject initiates a trial, flow proceeds to block 1508.

At block 1508, a stimulus stream is created from the current stimulus set, for the current processing level. Once the stimulus stream is created, it is played for the subject, as illustrated in FIGS. 9–11. Flow then proceeds to decision block 1510.

At decision block 1510, a determination is made as to whether the subject has correctly identified the target. Recall that the target word is properly identified when the subject presses down the mouse button within 1000 ms of the time the target word is played. If the subject does not properly identify the target, either because he/she failed to signal selection of the target word within the hit window, or because he/she incorrectly selected a distractor word, flow proceeds to decision block 1512. Otherwise, flow proceeds to decision block 1516.

At decision block 1512, a determination is made as to whether the subject has responded incorrectly to less than 70% of the last 20 trials. If this is true, then further testing of the present stimulus set is temporarily discontinued, and flow proceeds to block 1528. If the subject has correctly responded to 70% or more of the last 20 trials, flow proceeds to decision block 1514.

At decision block 1514, a determination is made as to whether the subject has initiated more than 30 trials for the current stimulus set, at the current processing level. If not, then flow proceeds back to decision block 1506 to await another trial. However, if the subject has engaged in more than 30 trials, flow proceeds to block 1528.

At block 1528, the stimulus set for the trials is incremented. Thus, if the current stimulus set is 1, the next stimulus set for trials will be 2. It is believed that for whatever reason, if the subject reaches block 1528 from either decision block 1512 or 1514, it is because they are having particular difficulty with the target word in the current stimulus set. So, rather than continuing testing with that target word, the current stimulus set is left open for later testing, and a new stimulus set is selected. Flow then proceeds back to decision block 1506 for initiation of another trial using the new stimulus set.

At decision block 1516 a determination is made as to whether the subject has correctly responded to 4 out of the last 5 trials. If not, then flow proceeds back to decision block 1506 for another trial. However, if the subject has correctly responded to 4 out of the last 5 trials, flow proceeds to decision block 1518. The 4 out of 5 criterion relies on the binomial probability that the subject did not attain this performance level by chance with a 95% probability.

At decision block 1518, a determination is made as to whether the maximum stage for the current stimulus set, for the current processing level, has been reached. As mentioned above, the current embodiment of the present invention includes 4 stages. If the current stage is not the last stage, then flow proceeds to block 1520. Otherwise, flow proceeds to decision block 1526.

At block 1520, the current stage is incremented. Thus, if the current stage is 1, the next stage will be set to 2. This configures the game to utilize a different distractor word, or set of distractor words for the current target word. Flow then proceeds to decision block 1522.

At decision block 1522, a test is made as to whether the current stage is the last stage for the current stimulus set at the current processing level. If not, then flow proceeds back to decision block 1506 for initiation of another trial. Otherwise, flow proceeds to block 1524.

At block 1524 a reward play is provided. In one embodiment of Polar Cop, three different reward plays are provided. The reward plays are slowly introduced to a subject, over a period of time, to reward a subject for his/her continued diligence and success with the game.

Referring briefly to FIG. 16, a screen 1600 is shown of one of the reward plays provided within Polar Cop. The screen 1600 shows an igloo 1603 with a number of windows 1605. An informant 1601 creeps onto the screen 1600, and upon initiation by the subject, provides a visual (grapheme) and aural (word) clue to the subject. At this point, a stimulus stream begins, at the current processing level, at the current stage. However, instead of character's proceeding thru a snowy landscape, they pop out of the windows 1605, as shown by the character 1607. If the subject correctly identifies the target word, a grapheme 1609 associated with the target word is presented, and tossed into a getaway vehicle 1611. After successfully completed a trial, a number of penguin burglars exit the building, hop into the getaway vehicle 1611, and the getaway vehicle 1611 speeds away with a polar cop in hot pursuit. Referring back to FIG. 15, after the reward play is completed, flow proceeds back to decision block 1506 for initiation of another trial.

At block 1526, a determination is made as to whether the current stimulus set is the last set to be tested. That is, is the current stimulus set equal to 62? If not, flow proceeds to block 1528. Otherwise, flow proceeds to decision block 1530.

At block 1528, the stimulus set is incremented. For example, if the current stimulus set is equal to 1, the stimulus set will be incremented to 2. In addition, the current stage will be reset to 1. Flow then proceeds back to decision block 1506 for initiation of another trial using the new stimulus set.

At decision block 1530, a determination is made as to whether all of the stimulus sets have been closed. That is, has the subject correctly progressed through all 4 stages of all 62 stimulus sets at the current processing level, within the current phase? If so, then flow proceeds to decision block 1534. Otherwise, flow proceeds to block 1532.

At block 1532, the stimulus set is set equal to the next open set. Recall that if a subject causes the program to proceed to block 1528 from either decision block 1512 or 1514, then the stimulus set is changed even though the subject has not correctly identified the target word in 4 out of 5 trials. So, even though the stimulus set is allowed to change, at block 1528, the subject cannot progress past decision block 1530 until the subject has mastered all of the stimulus sets at the current processing level. The stage is also reset to 1. Flow then proceeds back to decision block 1506 for initiation of another trial.

At decision block 1534, a determination is made as to whether the current training phase is Phase II. If not, flow proceeds to block 1536. Otherwise, flow proceeds to decision block 1538.

At block 1536, the phase is incremented (set to Phase II), the stimulus set is reset to 1, and the stage is set to 1. Thus, after a subject correctly responds to all 4 stages of all 62 stimulus sets, at the current processing level, the phase is changed, and training begins again with stimulus set 1, stage 1. Flow then proceeds back to decision block 1506 for initiation of another trial.

At decision block 1538 a determination is made as to whether the current processing level is the last processing level. As mentioned above, the present embodiment includes processing levels 1–3. If the current processing level is not the last processing level, then flow proceeds to block 1540. Otherwise, the subject has correctly responded to all 4 stages, for all 62 stimulus sets, for each phase, for all processing levels. At this point, flow proceeds to block 1542 where training is completed.

At block 1540, the current processing level is incremented. Thus, if the current processing level is 1 (20 dB emphasis), then it is incremented to Level 2 (10 dB emphasis). In addition, the phase is reset to 1, the stimulus set is reset to 1, and the stage is reset to 1. Thus, a subject reaches block 1540 after successfully responding to all stages of all stimulus sets for all phases, within a given processing level. Block 1540 decreases the amount of processing applied to the stimulus sets, and training begins again at decision block 1506. Once a subject proceeds thru all stages of all stimulus sets, for all phases, at all processing levels, the game is completed.

The flow chart 1500 thus describes a particular embodiment of the present invention for adaptively training a subject to distinguish between similar sounding words, whether the target word is in the front, middle or end of a word, and to associate particular words with their representative graphemes.

Although the present invention and its objects, features, and advantages have been described in detail, other embodiments are encompassed by the invention. For example, the methodology of the present invention has been described with reference to a particular game story entitled Polar Cop. It should be appreciated that the story line for the game is inconsequential to the methodology used to train a subject in word/grapheme recognition. While the story line of the game should be engaging and entertaining, other story lines, game scenarios, etc., could be used.

In addition, a particular strategy has been shown in FIG. 15 for adaptively altering stimulus sets, processing levels, reward plays, etc., based on a subject's performance. Other performance criteria could be used to modify trial sequencing, without departing from the training methodology encompassed by the present invention.

Furthermore, the stimulus sets shown in Appendix A are not exhaustive. Rather, it is believed that they provide significant training for a subject, given particular time constraints on game play imposed by the market. However, additional or alternative stimulus sets are anticipated by the inventors.

Moreover, only 3 speech processing levels have been described for enhancing word recognition. It should be appreciated that additional or alternative speech processing could be used to further enhance a subjects neurological training. Such speech processing could include time expansion, as well as frequency component emphasis, of selected words, and could include varying the Inter-Stimulus-Interval between presented words.

Finally, the Polar Cop program has been shown for execution on a personal computer, connected to a central server. However, as technology advances, it is envisioned that the program could be executed either by a diskless computer attached to a server, by a handheld processing device, such as a laptop, or eventually by a palmtop device such as a Nintendo GameBoy. As long as the graphical images and auditory prompts can be presented in a timely fashion, and with high quality, the nature of the device used to present the material is irrelevant.

Those skilled in the art should appreciate that they can readily use the disclosed conception and specific embodiments as a basis for designing or modifying other structures for carrying out the same purposes of the present invention without departing from the spirit and scope of the invention as defined by the appended claims.

APPENDIX A

| Stim. set | rhyme target | foil a | foil b | foil c |
|---|---|---|---|---|
| CVC's target change, rhyme constant | | | | |
| B's with different vowels | | | | |
| 1 | bib | sib | fib | rib |
| 2 | big | dig | pig | jig |
| 3 | bad | dad | pad | mad |
| 4 | bat | pat | cat | sat |
| 5 | bug | dug | tug | rug |
| 6 | but | put | cut | nut |
| 7 | bog | dog | hog | log |
| D's with different vowels | | | | |
| 8 | dig | big | pig | rig |
| 9 | dab | gab | cab | jab |
| 10 | dub | tub | cub | rub |
| 11 | dug | bug | jug | mug |
| 12 | dot | got | pot | not |
| G's with different vowels | | | | |
| 13 | gab | cab | jab | lab |
| 14 | gap | tap | cap | map |
| 15 | got | dot | pot | hot |
| P's with different vowels | | | | |
| 16 | pig | big | rig | wig |
| 17 | pit | bit | sit | mit |
| 18 | pat | bat | sat | hat |
| 19 | pet | get | jet | net |
| 20 | pop | top | cop | hop |
| 21 | pub | tub | cub | sub |
| T's with different vowels | | | | |
| 22 | tip | dip | rip | hip |
| 23 | tad | bad | sad | fad |
| 24 | tap | gap | cap | map |
| 25 | top | pop | cop | mop |
| 26 | tug | dug | bug | jug |
| K | | | | |
| 27 | kit | pit | lit | fit |
| C's with different vowels | | | | |
| 28 | cab | gab | tab | lab |
| 29 | cat | bat | pat | mat |
| 30 | cod | god | pod | mod |
| 31 | cot | dot | got | pot |
| 32 | cut | but | mut | nut |
| CVCCs onset change, rhyme constant | | | | |
| ck final | | | | |
| 33 | back | pack | tack | jack |
| 34 | deck | peck | neck | heck |
| 35 | dock | tock | jock | sock |
| 36 | pack | back | lack | rack |
| 37 | pick | tick | kick | sick |
| 38 | puck | buck | duck | luck |
| 39 | tick | pick | kick | wick |
| 40 | tuck | duck | buck | luck |
| sh final | | | | |
| 41 | bash | dash | cash | gash |
| 42 | dash | bash | mash | rash |
| 43 | gash | cash | sash | lash |
| 44 | gush | hush | rush | lush |
| st final | | | | |
| 45 | best | pest | west | rest |
| 46 | dust | bust | rust | lust |
| 47 | gust | bust | dust | must |
| 48 | pest | best | nest | rest |
| 49 | test | best | pest | rest |
| B's with different vowels | | | | |
| 50 | bib | bid | big | bick |
| 51 | bed | bet | beg | best |
| D's with different vowels | | | | |
| 52 | dab | dad | dan | dash |
| 53 | dog | doc | dot | dock |
| G's with different vowels | | | | |
| 54 | gag | gap | gas | gash |
| 55 | gut | gum | gun | gush |

APPENDIX A-continued

| Stim. set | rhyme target | foil a | foil b | foil c |
|---|---|---|---|---|
| P's with different vowels | | | | |
| 56 | pet | peg | pen | peck |
| 57 | pot | pop | pod | posh |
| T's with different vowels | | | | |
| 58 | tap | tag | tan | tack |
| 59 | top | tot | tom | tock |
| K | | | | |
| 60 | ked | keg | ken | kept |
| C's with different vowels | | | | |
| 61 | cab | cap | cat | cash |
| 62 | cub | cup | cut | cud |

What is claimed is:

1. A method for adaptively developing neural activity, to improve signal differentiation in spoken language, the method utilizing speech processing for enhancing a subject's ability to distinguish between similar phonemes, the method using a plurality of stimulus sets, each of the stimulus sets having a target phoneme, and a plurality of distractor phonemes, the method comprising:
   a) indicating a processed target phoneme from one of the plurality of stimulus sets;
   b) presenting a stimulus sequence to a subject, the stimulus sequence having the processed target phoneme within a plurality of distractor phonemes from the one of the plurality of stimulus sets;
   c) if the subject signals identification of the processed target phoneme, recording the identification as correct;
   d) repeating a)–c); and
   e) adaptively selecting an alternate stimulus set for presentation to the subject based on the subject's performance.

2. The method for adaptively developing neural activity, as recited in claim 1 wherein the speech processing emphasizes selected stop consonants before they are presented to a subject.

3. The method for adaptively developing neural activity, as recited in claim 2 wherein 0–20 dB of emphasis is applied to the selected stop consonants to provide a plurality of processing levels.

4. The method for adaptively developing neural activity, as recited in claim 1 wherein the plurality of stimulus sets include CVC and/or CVCC phonemes.

5. The method for adaptively developing neural activity, as recited in claim 1 wherein the plurality of distractor phonemes within the plurality of stimulus sets are phonetically similar to the target phoneme within their associated stimulus set.

6. The method for adaptively developing neural activity, as recited in claim 1 wherein a) comprises:
   a1) aurally playing the processed target phoneme to the subject; and
   a2) graphically displaying a grapheme, corresponding to the processed target phoneme.

7. The method for adaptively developing neural activity, as recited in claim 1 wherein the target phoneme does not occur within a first position within the stimulus sequence.

8. The method for adaptively developing neural activity, as recited in claim 1 wherein the target phoneme is randomly placed within the plurality of distractor phonemes.

9. The method for adaptively developing neural activity, as recited in claim 1 wherein one or more of the plurality of distractor phonemes is used to create the stimulus sequence.

10. The method for adaptively developing neural activity, as recited in claim 1 wherein the processed target phoneme and each of the plurality of distractor phonemes within the stimulus sequence are separated from each other by a predetermined amount of time.

11. The method for adaptively developing neural activity, as recited in claim 1 wherein b) comprises:
    b1) playing each phoneme within the stimulus sequence, one at a time, for the subject.

12. The method for adaptively developing neural activity, as recited in claim 11 wherein b) further comprises:
    b2) graphically presenting a character, along with each phoneme that is played, to visually cue the subject to signal identification.

13. The method for adaptively developing neural activity, as recited in claim 12 wherein the subject signals identification by pressing a mouse button.

14. The method for adaptively developing neural activity, as recited in claim 1 wherein the subject signals identification of the processed target phoneme by placing a cursor over the character and pressing a mouse button.

15. The method for adaptively developing neural activity, as recited in claim 1 wherein the subject must signal identification of the processed target phoneme within a predetermined time window.

16. The method for adaptively developing neural activity, as recited in claim 15 wherein the predetermined time window starts after the processed target phoneme is played, and ends before a next distractor phoneme is played.

17. The method for adaptively developing neural activity, as recited in claim 1 wherein c) records the correct identification in a data file.

18. The method for adaptively developing neural activity, as recited in claim 17 wherein the data file maintains a record of correct identifications for each of the plurality of stimulus sets.

19. The method for adaptively developing neural activity, as recited in claim 1 wherein c) further comprises:
    c1) if the subject does not signal identification of the processed target phoneme, recording the identification as incorrect.

20. The method for adaptively developing neural activity, as recited in claim 19 further comprising:
    f) if the subject correctly identifies less than 70% of processed target phonemes after a predetermined number presented stimulus sequences, selecting an alternate stimulus set for presentation to the subject.

21. The method for adaptively developing neural activity, as recited in claim 1 further comprising:
    f) if the subject obtains the predetermined number of correct identifications in g), for each of the plurality of stimulus sets, reducing an amount of processing applied to the target phoneme in b).

* * * * *